United States Patent [19]

Christensen et al.

[11] 4,218,462
[45] Aug. 19, 1980

[54] 6-(1-HYDROXYETHYL)-2-(2-AMINOETHYL-THIO)-1-SUBSTITUTED-1-CARBADE-THIAPEN-2-EM-3-CARBOXYLIC ACIDS

[75] Inventors: Burton G. Christensen, Metuchen; David H. Shih, Edison, both of N.J.

[73] Assignee: Merck & Co., Inc., Rahway, N.J.

[21] Appl. No.: 954,270

[22] Filed: Oct. 24, 1978

[51] Int. Cl.² .................. C07D 487/04; A61K 31/40
[52] U.S. Cl. .............. 424/274; 260/245.2 T; 260/239 A; 260/559 T; 542/413; 542/416; 544/92; 560/16; 560/21; 560/205; 560/210
[58] Field of Search .................... 260/326.31; 424/274

[56] References Cited
U.S. PATENT DOCUMENTS
3,950,357  4/1976  Kahan et al. .................... 260/326.31

OTHER PUBLICATIONS
Johnston et al., J.A.C.S. p 313 (1978).

Primary Examiner—Mary C. Lee
Attorney, Agent, or Firm—James A. Arno; Julian S. Levitt

[57] ABSTRACT

Disclosed are 1-substituted-6-(1-hydroxyethyl)-2-(2-aminoethylthio)-1-carbadethiapen-2-em-3-carboxylic acids (I) and their pharmaceutically acceptable salts and esters which are useful as antibiotics; such compounds are prepared by total synthesis.

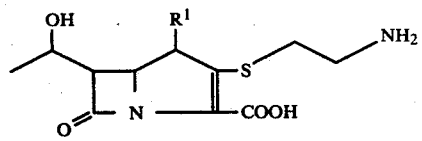

wherein $R^1$ is, inter alia, substituted and unsubstituted alkyl, aryl and aralkyl.

15 Claims, No Drawings

6-(1-HYDROXYETHYL)-2-(2-AMINOETHYLTHIO)-1-SUBSTITUTED-1-CARBADE-THIAPEN-2-EM-3-CARBOXYLIC ACIDS

BACKGROUND OF THE INVENTION

This invention relates to 6-(1-hydroxyethyl)-2-(2-aminoethylthio)-1-substituted-1-carbadethiapen-2-em-3-carboxylic acids (I) and their pharmaceutically acceptable salts and esters which are useful as antibiotics. This invention also relates to a process for preparing such compounds, (I):

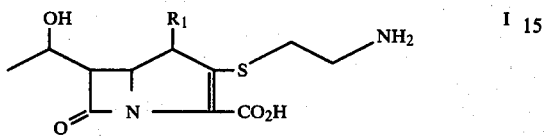

wherein $R^1$ is selected from the group consisting of substituted and unsubstituted loweralkyl having from 1-6 carbon atoms, aralkyl; such as phenyl loweralkyl; aryl such as phenyl; cycloalkyl having from 3-6 carbon atoms; and cycloalkylalkyl having 1-3 carbon atoms in the alkyl moiety and 3-6 carbon atoms in the ring; wherein said ring or chain substituents are $R^1$ are selected from the group consisting of hydroxyl, chloro, bromo, fluoro, amino, mono-, di-, and trialkylamino wherein the alkyl moiety has 1-6 carbon atoms; carboxyl, carbamoyl, ureido, amidino, guanidino and the like.

There is a continuing need for new antibiotics. For unfortunately, there is no static effectiveness of any given antibiotic because continued wide scale usage selectively gives rise to resistant strains of pathogens. In addition, the known antibiotics suffer from the disadvantage of being effective only against certain types of microorganisms. Accordingly the search for new antibiotics continues.

Thus, it is an object of the present invention to provide a novel class of antibiotics which are useful in animal and human therapy and in inanimate systems. These antibiotics are active against a broad range of pathogens which representatively include both gram positive bacteria such as *S. aureus, Strep. pyogenes* and *B. subtilis,* and gram negative bacteria such as *E. coli, Proteus morganii, Pseudomonas,* Serratia and Klebsiella. Further objects of this invention are to provide chemical processes for the preparation of such antibiotics and their non-toxic pharmaceutically acceptable salts; pharmaceutical compositions comprising such antibiotics; and to provide methods of treatment comprising administering such antibiotics and compositions when an antibiotic effect is indicated.

DETAILED DESCRIPTION OF THE INVENTION

The total synthesis of the present invention which provides the compounds of the present invention (I) may conveniently be summarized by the following reaction diagram:

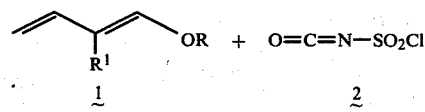

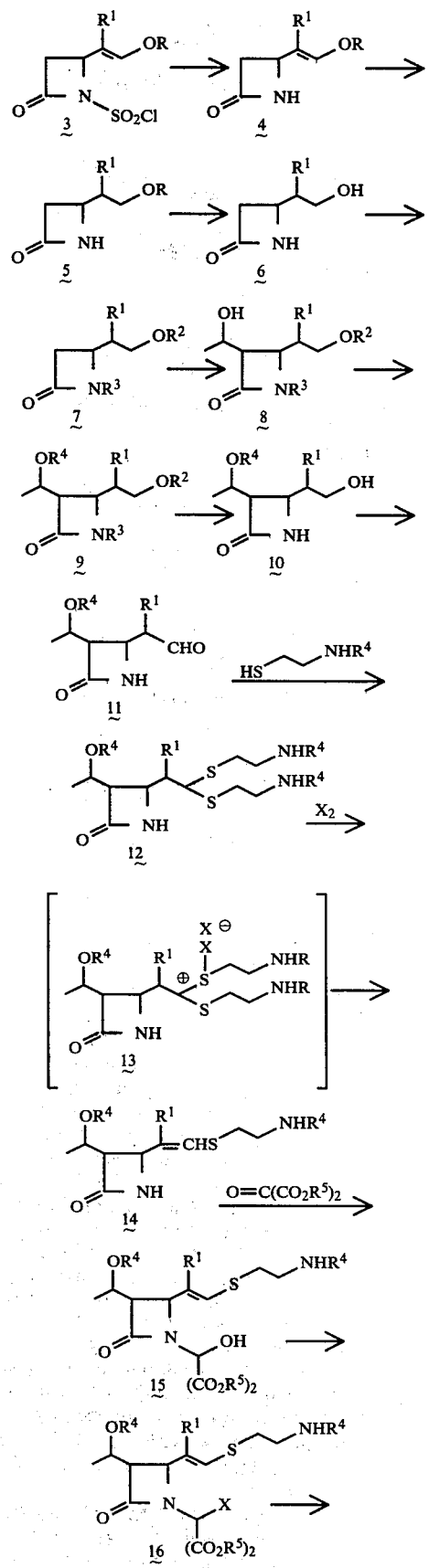

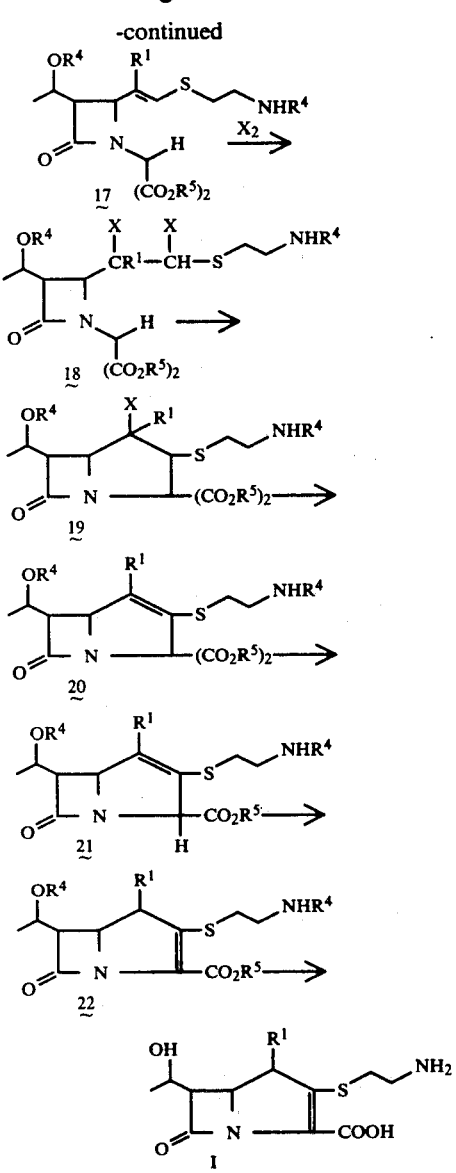

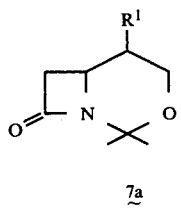

or the like at 0° to 25° C. from 5 minutes to 2 hours under 1 to 10 atmospheres of hydrogen in the presence of a hydrogenation catalyst such as a platinum metal or oxide thereof such as 10% Pd/C or the like.

The de-blocking reaction 5→6 is usually desirable when R is acyl to permit the later alkylation 7→8. The preferred de-blocking procedure is by alcoholysis wherein the solvent is a lower alkanol such as methanol, ethanol or the like in the presence of the corresponding alkali metal alkoxide, such as sodium methoxide. Typically, the reaction is conducted for from 5 minutes to 1 hour at a temperature of from −10° to 25° C.

Blocking groups $R^3$ and $R^2$ are established (6→7) to provide a suitably protected species for alkylation (7→8). There is no criticality in the choice of blocking groups, provided only that they do not interfere with the intended alkylation. $R^3$ may be hydrogen, a triorganosilyl group such as trimethylsilyl, t-butyldimethylsilyl or the like, or a cyclic ether such as 2-tetrahydropyranyl; $R^2$ may be also be a cyclic ether such as 2-tetrahydropyranyl or t-butyldimethylsilyl; alternatively $R^3$ and $R^2$ may be joined together to form protected species such as 7a:

For example, species such as 7a are conveniently prepared by treating 6 with 2,2-dimethoxypropane in the presence of a catalyst such as boron trifluoride etherate, toluene sulphonic acid, or the like in a solvent such as methylene chloride, ether, chloroform, dioxane or the like at a temperature of from −10° C. to 35° C. for from a few minutes to 1 hour.

The alkylation (7→8) is preferably conducted by treating 7 with a strong base such as lithium diisopropylamide, sodium amide, potassium hydride or the like in a solvent such as THF, glyme, ether, dimethylformamide (DMF), dimethylsulfoxide (DMSO) or the like at a temperature of from −78° C. to 0° C. The resulting anion is then treated with excess acetaldehyde to provide 8.

The reaction 8→9 establishes the blocking group $R^4$ and is typically accomplished by treating 8 with a base such as an alkali metal hydroxide, lithium diisopropyl amide 4-dimethylaminopyridine, or n-butyllithium in a solvent such as ether, THF, dioxane, DMF, DMSO or the like, followed by treatment with an acyl halide of choice such as an alkanoyl, aralkanoyl or nuclear substituted aralkanoyl, or alkyl, aryl or aralkyl, substituted aralkyl or substituted aryl haloformate such as p-nitrobenzylchloroformate or the like at a temperature of from −78° C. to 25° C. for from 1-24 hours.

The de-blocking reaction 9→10 is typically conducted by acid hydrolysis such as aqueous acetic acid at a temperature of from 25° C. to 75° C. for from 5 minutes to 3 hours.

The aldehyde intermediate 11 is prepared by treating 10 with an oxidizing agent such as $CrO_3$.2 (pyridine) in $CH_3CN$, pyridium chlorochromate in $CH_2Cl_2$, 1:1 mixture of dimethylsulfoxide and acetic anhydride, cy- In words relative to the above diagram, the 4-(1,2-substituted -vinyl)azetidin-2-one, 4, starting material is prepared by reacting an $R^1$-, R-substituted oxybutadiene, 1, with chlorosulfonylisocyanate 2. The reaction is conducted without solvent or may be run in solvent such as diethyl ether, ethyl acetate, chloroform, methylene chloride, or the like at a temperature of from −78° C. to 25° C. for from a few minutes to 1 hour to provide 3. The radical $R^1$ is as defined above for structure I; the radical R is an easily removable acyl blocking group such as an alkanoyl or aralkanoyl which bears no functional group or groups which might interfere with the desired course of reaction (1+2→3→4). Intermediate species 3 is converted to the sulfinamide by reduction which is then hydrolyzed to 4 at pH 6-8. Typically the reaction solution comprising 3 is contacted (5-30 minutes) with an aqueous solution (at 0°-25° C.) of a reducing agent such as sodium sulfite, thiophenol, or the like, at pH 6-8 to provide 4.

The reaction 4→5 is a reduction, and is preferably achieved by hydrogenation in a solvent such as ethyl acetate, ether, dioxane, tetrahydrofuran (THF), ethanol clohexylcarbodiimide in DMSO or the like at a temperature of from 9°–25° C. for from 5 minutes to 1 hour. The resulting species $\underline{11}$ in a solvent such as acetonitrile, methylene chloride, chloroform or the like at a temperature of from −10° to 25° C. is treated with an excess of N-blocked cysteamine, $HSCH_2\text{-}CH_2NHR^4$, in the presence of an acid catalyst such as boron trifluoride etherate, toluene sulphonic acid or the like to provide $\underline{12}$. Typically, the reaction requires from 1 to 60 minutes. There is no criticality as to the identity of the N-protecting group, $R^4$, or the cysteamine reagent and suitable groups are p-nitrobenzyloxycarbonyl, o-nitrobenzyloxycarbonyl, t-butyloxycarbonyl, 2,2,2-trichloroethoxycarbonyl, phthaloyl, or the like.

The vinyl sulphide $\underline{14}$ is obtained via intermediate $\underline{13}$ by treating $\underline{12}$ with a halogen such as chlorine or bromine (X=Cl or Br) in a solvent such as ether, methylene chlorine, tetrahydrofuran, glyme or the like at a temperature of from −78° to 30° C. for from 1 to 30 minutes, followed immediately by treating with an olefin such as cyclohexene, isobutylene, or the like in the presnece of base such as triethylamine, DBU, sodium hydride, or the like in a solvent such as DMF, glyme, THF, HMPA. The solution is held at −20° to 25° C. for from 1 to 8 hours to yield $\underline{14}$.

The vinyl sulphide species $\underline{14}$ is reacted with a diester of oxomalonic acid (or its monohydrate) to provide $\underline{15}$. There is no criticality as to the identity of the ester moiety, $R^5$, of the oxomalonic acid. $R^5$ may be a conventional, easily removable blocking group or it may be a pharmaceutically acceptable ester moiety. Suitable ester radicals $R^5$ are p-nitrobenzyl, benzyl, o-nitrobenzyl, t-butyl, 2,2,2-trichloroethyl. The reaction $\underline{14}\rightarrow\underline{15}$ is typically conducted in a high boiling organic solvent such as benzene, toluene, cyclohexane, halo aromatic or the like at a temperature of from about 50° C. to reflux for from 0.5 to 6 hours.

The halogenation reaction $\underline{15}\rightarrow\underline{16}$ is typically conducted in a solvent such as THF, glyme, ether, methylene chloride, chloroform or the like in the presence of a hlaogenating agent such as thionyl chloride, phosphorous pentachloride or the like in the presence of base such as pyridine at a temperature of from −20° to 25° C. for from 5 minutes to 3 hours. The selective reduction of $\underline{15}\rightarrow\underline{17}$ via $\underline{16}$ is completed by treating $\underline{16}$ with tributylphosphine, triphenylphosphine or the like in aqueous DMF or similar aqueous systems involving dioxane, THF, glyme, DMSO, or acetone at a temperature of from about 0°–50° C. for from 10 minutes to 5 hours.

Species $\underline{17}$ is halogenated by the previous procedure ($\underline{12}\rightarrow\underline{13}$), but omitting the addition of the cyclohexene or other olefin, to provide the dihalo species $\underline{18}$. Species $\underline{18}$ is treated with a base such as triethylamine, sodium hydride or potassium hydride in a solvent such as DMF, acetonitrile, methylene chloride, chloroform, glyme or the like at a temperature of from about −78° to 25° C. for 1 to 5 hours to provide $\underline{19}$. Species $\underline{19}$ is converted to $\underline{20}$ on treatment with a strong base such as 1,5-diazabicyclo[5.4.0]undec-5-ene(DBU), 1,5-diazabicyclo[3.4.0]non-5-ene(DBN), or the like in a solvent such as DMSO, acetone, chloroform, DMF, THF, glyme or the like or on treatment with AgF in pyridine at a temperature of from 0°–40° C. for from ¼ to 24 hours. The reaction $\underline{20}\rightarrow\underline{21}$ is conducted by treating $\underline{20}$ with an aromatic base such as pyridine, s-collidine or lutidine, in the presence of a displacing agent such as lithium iodide, lithium bromide, sodium bromide, or the like at a temperature of from about 80°–150° C. for from 15 minutes to 2 hours. An aqueous work up of the resulting reaction mixture provides $\underline{21}$. Isomerization of the double bond $\underline{21}\rightarrow\underline{22}$ is accomplished by treating $\underline{21}$ in a solvent such as DMF, DMSO, ethyl ether, THF, glyme, methylene chloride with a strong base such as diisopropylamine, DBU, DBN, or the like at a temperature of from 0° to about 25° C. for from a few minutes to 2 hours or until equilibrium has been established as determined by examination of sample aliquots by ultraviolet absorption or by thin layer chromatography. The final reaction $\underline{22}\rightarrow\underline{I}$(by hydrogenolysis of the blocking groups) is accomplished by treating $\underline{22}$ in a solvent such as dioxane, ethanol, THF or the like or an aqueous mixture thereof in the presence of a platinum metal catalyst such as Pd/C under a hydrogen pressure of from 1–4 atmospheres for from 0.5 to 8 hours at a temperature of from about 0°–25° C.

SEPARATION OF ISOMERS

Because of the four (possibly more, depending on the nature of $R^1$) centrers of asymmetry, the compounds of structure I, above, are capable of existing in at least sixteen isomeric forms.

The above-described total synthesis may be conducted in such a manner that all isomers are ultimately obtained as a mixture, or it may be conducted in a stereo-selective way. Such stereo-selective approaches involve separation of diastereoisomers in the chain of synthesis such as at the $\underline{7}$, $\underline{8}$ and $\underline{9}$ level. In any event, a give isomeric mixture of I may be resolved into its constituent isomers by application of any of a variety of well-known techniques. For example, in the simplest case, the eight diastereomers may be separated by chromatography and any given racemic pair of optical isomers may be separated by any of a variety of physicochemical techniques after forming diastereomeric salts with an optically active acid or base. A representative illustration of such separations technique is given below in the Examples section.

Especially preferred embodiments of the present invention are those wherein $R^1$ is selected from the group consisting of methyl, ethyl, propyl, isopropyl, cyclopropyl, phenyl, benzyl, and 2-bromoethyl.

The compounds made available by the present invention are valuable antibiotics active against various gram-positive and gram-negative bacteria and, accordingly, find utility in human and veterinary medicine. Such sensitive bacteria representatively include: *Staphylococcus aureus, Escherichia coli, Klebsiella pneumoniae, Serratia, Salmonella typhosa, Pseudomonas* and *Bacterium proteus*. The resulting compounds may further be utilized as additives to animal feed, for preserving foodstuffs, and as disinfectants. For example, they may be employed in aqueous compositions in concentrations ranging from 0.1 to 100 parts of antibiotic per million parts of solution in order to destroy and inhibit the growth of harmful bacteria on medical and dental equipment and as bactericides in industrial applications, for example, in waterbased paints and in the white water of paper mills to inhibit the growth of harmful bacteria.

These antibiotics may be used alone or in combination as an active ingredient in any one of a variety of pharmaceutical preparations. These antibiotics and their corresponding salts may be employed in capsule form or as tablets, powders or liquid solutions or as suspensions or elixirs. They may be administered orally, intravenously or intramuscularly.

Tablets and capsules for oral administration may be in unit dose presentation form, and may contain conventional excipients such as binding agents, for example, syrup, acacia, gelatin, sorbitol, tragacanth, or polyvinylpyrrolidone; fillers for example, lactose, sugar, maize-starch, calcium phosphate, sorbitol or glycine; lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparations may be in the form of aqueous or oily suspension, solution, emulsions, or syrups; or may be presented as a dry product, for reconstitution with water or other suitable vehicles before use. Such liquid preparations may contain conventional additives such as suspending agents, for example, sorbitol, syrup, methyl cellulose, glucose/sugar syrup, gelatin, hydroxyethylcellulose, carboxymethyl cellulose, aluminum stearate gel or hydrogenated edible oils, for example almond oil, fractionated coconut oil, oily esters, propylene glycol, or ethyl alcohol; preservatives, for example methyl or propyl p-hydroxybenzoates or sorbic acid.

Compositions for injection may be presented in unit dose form in ampules, or in multidose container. The compositions may take such forms as suspensions, solutions, or emulsions in oily or aqueous vehicles, and may contain formulatory agents such as suspending, stabilizing and/or dispersing agents. Alternatively, the active ingredient may be in powder form for reconstitution with a suitable vehicle, e.g., sterile, pyrogen-free water, before use.

The compositions may also be prepared in suitable forms for absorption through the mucous membranes of the nose and throat or bronchial tissues and may conveniently take the form of powder, liquid sprays, inhalants, lozenges, or throat paints. For medication of the eyes or ears, the preparations may be presented as individual capsules, in liquid or semi-solid form, or may be used as drops etc. Topical applications may be formulated in hydrophobic or hydrophilic bases as ointments, creams, or lotions.

Also, in addition to a carrier, the instant compositions may include other ingredients such as stabilizers, binders, antioxidants, preservatives, lubricators, suspending agents, viscosity agents or flavoring agents and the like. In addition, there may also be included in the compositions other active ingredients to provide a broader spectrum of antibiotic activity.

For veterinary medicine the composition may, for example, be formulated as an intramammary preparation in either long or quick-release bases.

The dosage to be administered depends to a large extent upon the general health and weight of the subject being treated, and the route and frequency of administration—the parenteral route being preferred for generalized infections and the oral route for intestinal infections. In general, a daily oral dosage consists of from about 2 to about 600 mg. of active ingredient per kg. of body weight of the subject in one or more applications per day. A preferred daily dosage for adult humans lie in the range of from about 15 to 150 mg. of active ingredient per kg. of body weight.

The instant compositions may be administered in several unit dosage forms as, for example, in solid or liquid orally ingestible dosage form. The compositions per unit dosage, whether liquid or solid may contain from 0.1% to 99% of active material, the preferred range being from about 10–60%. The composition will generally contain from about 15 mg. to about 1500 mg. of the active ingredient; however, in general, it is preferably to employ a dosage amount in the range of from about 100 mg. to 1000 mg. In parenteral administration the unit dosage is usually the pure compound in a slightly acidified sterile water solution or in the form of a soluble powder intended for solution.

Especially preferred pharmaceutically acceptable salts and esters involving the carboxyl group of compounds of the present invention (I) are disclosed and claimed in U.S. Patent Application Ser. No. 861,314 (filed Dec. 16, 1977) which application is directed, inter alia, to pharmaceutically acceptable salts and esters of the carboxyl group of thienamycin. It is precisely these salts and esters which are preferred in the present invention and they are prepared in a manner analogous to that disclosed in U.S. Patent Application Ser. No. 861,314, which is incorporated herein by reference. Thus, especially preferred salts include sodium, potassium, ammonium, and the like; and especially preferred esters include pivaloxymethyl, p-t-butylbenzyl, 5-indanyl, 3-phthalidyl, 3-methyl-2-butenyl, and the like. One should note that when, in the total synthesis outlined above, $R^2$ is a pharmaceutically acceptable ester moiety, there is no need for the final deblocking step if it is desired to have the final product I in the form of a pharmaceutically acceptable ester.

Especially preferred embodiments of the present invention are those, as defined above, except that the amino group on the aminoethylthio side chain of Structure I is derivatized according to the teachings of Belgium Patent No. 848,545 (issued May 20, 1977); the resulting amino group being represented thusly (partial structure):

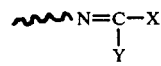

wherein X and Y are defined by the publication; species wherein X is H or lower alkyl and Y is $NH_2$ are especially preferred.

The following Examples illustrate but do not limit the product, process, compositional or method of treatment aspects of the present invention. All reaction temperatures are in °C.

EXAMPLE 1

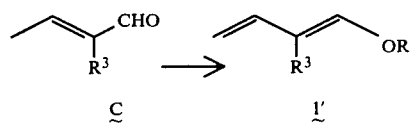

The $\alpha,\beta$-unsaturated aldehydes (C) are prepared by modified procedures reported by M. B. Green and W. J. Hickinbottom in *J. Chem. Soc.* 3262 (1957); and W. J. Bailey and R. Barclay, Jr., *J. Org. Chem.*, 21, 328 (1956).

Acetaldehyde (1 eq.) and propionaldehyde ($R^3$=CH$_3$) (1 eq.) are placed in a three-necked round-bottom flask which is equipped with a mechanical stirrer, a dry-ice condenser, and a pressure equalized dropping-funnel. To the solution is added dropwise 1 eq. of 1 N NaOH through the dropping funnel with constant stirring. After completion of the mixing, the mixture is stirred for 10 min, then poured into a beaker containing crushed ice. Extraction of the mixture with ether gives the crude product. The desired product (C) is obtained by fractional distillation through a Widmer column.

Isopropenyl acetate (2 eq), cuprous acetate (0.002 eq) p-toluenesulfonic acid (0.008 eq.) and the α,β-unsaturated aldehyde C (1 eq.) are placed in a three-necked round-bottom flask equipped with a thermometer, a nitrogen inlet tube and a Widmer column which is attached with a distillation head. The mixture is heated at 93°–110° C. until quantitative acetone is collected. The mixture is then allowed to cool to r.t. and filtered from solids. The dark brown filtrate is mixed with triethanolamine in water at 0° C. The two layer mixture is distilled quickly under reduced pressure. The organic layer of the distillate is separated. The aqueous layer is extracted with 200 ml ether. The combined organic layer is washed with 10% $K_2CO_3$, dried over $Na_2SO_4$, and evaporated in vacuo. The residue so obtained is mixed with 2.0 g N-phenyl-β-naphthamine and distilled under reduced pressure to give the desired 2-substituted 1-acetoxy-1,3-butadiene (1').

Following the procedure of Example 1, the following $R^3$ substituted species are obtained.

TABLE I

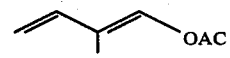

| $R^3$ | R |
|---|---|
| 1. $CH_3$ | $CH_3C\overset{O}{\underset{\|}{-}}$ |
| 2. $CH_3CH_2$ | $CH_3C\overset{O}{\underset{\|}{-}}$ |
| 3. $CH_3CH_2CH_2$ | $CH_3C\overset{O}{\underset{\|}{-}}$ |
| 4. $\begin{array}{c}CH_3\\ \phantom{C}\diagdown\\ \phantom{CH_3}CH\\ \phantom{C}\diagup\\ CH_3\end{array}$ | $CH_3C\overset{O}{\underset{\|}{-}}$ |
| 5. ▷– | $CH_3C\overset{O}{\underset{\|}{-}}$ |
| 6. Ph (Ph = phenyl) | $CH_3C\overset{O}{\underset{\|}{-}}$ |
| 7. $PhCH_2$ | $CH_3C\overset{O}{\underset{\|}{-}}$ |

EXAMPLE 2

Preparation of 6-(1-hydroxyethyl)-1-methyl-2-(2-aminoethylthio)-1-carbadethiapen-2-em-3-carboxylic acid

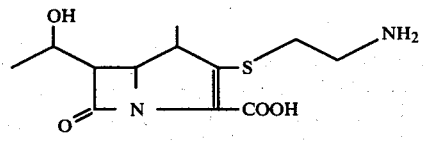

Step A

Preparation of 1'

Isopropenyl acetate (182 g), cupric acetate (0.40 g), 2-methyl-2-butenal (84 g) and p-toluenesulfonic acid (1.52 g) are placed in a 1.0-1, three-necked flask equipped with a thermometer, a nitrogen inlet tube and a 10-in. Widmer column which is attached with a distillation head. The mixture is heated at 93°–110° C. until 73 ml of acetone is collected. After cooling to r.t. (25° C.) the mixture is filtered from solids. The dark brown filtrate is cooled in an ice-bath and mixed with 3.4 g triethanolamine in 200 ml water. The two layer mixture is distilled quickly at 53 mm (b.p. 54° C.). The organic layer of the distillate is separated. The aqueous layer is extracted with 200 ml ether. The organic layers are combined and washed with 10% $K_2CO_3$, dried over $Na_2SO_4$, and evaporated in vacuo. The residue so obtained is mixed with 2.0 g N-phenyl-β-naphthamine and distilled under reduced pressure to give 1' (97 g), b.p. 81°–91° (66 mm).

Step B

Preparation of 2' and 3'

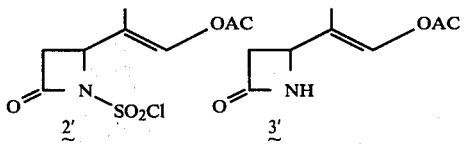

Chlorosulfonylisocyanate (CSI) (6.5 ml) is placed in a three-necked, 100-ml flask equipped with a thermometer, a magnetic stirring bar a nitrogen inlet tube and a 25-ml pressure-equalized dropping funnel. The CSI is chilled to −50° C. and mixed with 12.5 ml ether through the dropping funnel. The etheral solution of CSI is allowed to warm up to −25° C., to the solution is added dropwise 1-acetoxyl-2-methyl-1,3-butadiene (1') (5.9 ml in 12.5 ml ether) in 30 min. The mixture is then stirred for 20 min at −20°±3° C. The white precipitate formed initially is redissolved at the end of the reaction.

In a 500-ml round bottom flask, a solution of 10 g sodium sulfite and 25 g potassium hydrogen phosphate in 100 ml water is prepared and is cooled in an ice bath. Ether (100 ml) and crushed ice (100 g) are added and the mixture is vigorously stirred in an ice bath. At the end of 20 minutes reaction time, the reaction mixture which contains 2' is transferred into the dropping funnel and added dropwise to the hydrolysis mixture in 5 minutes. The hydrolysis is allowed to continue for an additional 30 minutes at 3° C. The organic layer is separated and the aqueous is extracted with 50 ml ether. The organic layers are combined, dried over $Na_2SO_4$ and evaporated to give crystalline product 3' (2.3 g), m.p. 77°–78,5°; m.s. 169 ($M^+$); IR 1760 $cm^{-1}$ (β-lactam); NMR (300 MHz, $CDCl_3$): 1.70 (d), 2.16 (s), 2.84 (qq), 3.18 (qq), 4.20 (m), 5.82 (broad, and 6.26 (s) ppm.

Step C

Preparation of 4'

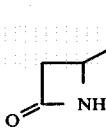

4-(1-methyl-2-acetoxyvinyl)azetidine-2-one (3') (6.5 g) is hydrogenated on a Parr shaker at r.t. under 40 psi hydrogen in the pressure of 10% Pc/C (0.6 g) in 200 ml ethylacetate for 2 hr. The mixture is filtered from the catalyst and the filtrate is evaporated in vacuo to give the crude product. Purification of the crude product by high pressure liquid chromatograph (HPLC) (silical gel column, 30% ethylacetate/CH$_2$Cl$_2$ solvent system) affords a white crystalline product 4' (6.04 g) after evaporation of solvent. The product shows following physical characteristics: ms 171 (M+); IR (Neat) 1754 cm$^{-1}$; NMR (60 MHz, CDCl$_3$): 0.96 (d), 1.01 (d), 2.06 (d, OAc), 2.75-3.80 (m), 3.99 (d) and 6.80 (broad) ppm.

STEP D

Preparation of 5'

Under N$_2$ at 0°, a solution of 4-(1-methyl-2-acetoxyethyl)-2-azetidinone 4' (1.2 g) in 10 ml methanol is treated with sodium methoxide (57 mg). After stirring for 1 hr, the solution is neutralized with glacial acetic acid (65 mg). Removal of methanol in vacuo gives crude 4-(1-methyl-2-hydroxyethyl)-2-azetidinone (5') as an oil. The product is purified chromatography on silica gel eluting with ethyl acetate and to give 0.78 g of 5':
IR (neat): 1740 cm$^{-1}$;
NMR (CDCl$_3$): 0.77 (d), 0.96 (d), 1.90 (m), 2.60–3.30 (m), 3.60 (m), 4.19 (s), and 7.23 (s). The product crystallizes as colorless solids in the refrigerator.

STEP E

Preparation of 6'

A solution of 4-(1-methyl-2-hydroxyethyl)-2-azetidinone (0.5 g) and 2,2-dimethoxypropane (0.48 g) in 10 ml anhydrous methylene chloride is treated with boron trifluoride (55 mg) at room temperature for 90 min. The mixture is washed with 5 ml saturated NaHCO$_3$. The organic layer is separated, dried over Na$_2$SO$_4$ and allowed to evaporate in vacuo to give crude isomeric mixture of 6' (0.48 g) as an oil.

Separation of isomers 6'α and 6'β is accomplished by high pressure liquid chromatography (HPLC) (silica gel) eluting with 40% ethylacetate/hexanes. After evaporation of the solvents affords 150 mg of 6'β as an oil and 200 mg of 6'α as a white solid.

NMR (300 MHz, CDCl$_3$) of 6'α: 0.81 (d), 1.31 (s), 1.68 (s), 1.62 (m), 2.52 (q), 3.05 (m), 3.42 (t), and 3.66 ppm (q), NMR (300 MHz, CDCl$_3$) of 6'β: 1.10 (d), 1.38 (s), 1.67 (s), 1.90 (m), 2.80 (q), 2.86 (q), 3.62 (q), 3.78 (m) and 3.98 (q) ppm.

STEP Fa

Preparation of 7'α

At −78° C., diisopropylamine (2.2 g) in 20 ml of anhydrous tetrahydrofuran is treated with n-butyllithium (1.6 M in n-hexane, 14 ml) for 5 min. To the solution is added 8-oxo-5α, 2,2-trimethyl-1-azabicyclo[4.2.0]octane (6'α) (3.4 g) and the mixture is stirred for 10 min. The resulting lithium enolate is treated with acetaldehyde (1.68 ml). The mixture is stirred for 1 min. then is quenched with 24 ml saturated ammonium chloride at −78° C., then allowed to warm to room temperature (25° C.). The mixture is extracted with ethylacetate (2×100 ml). The organic layer is separated, dried over Na$_2$SO$_4$ and allowed to evaporate in vacuo to give 4.5 g of the crude product 7'α.

The crude isomeric mixture of 7'α is purified and separated by HPLC (silica gel) eluting with 50% ethylacetate/methylene chloride to give 3.5 g of trans-7'α and 0.5 g of cis-7'α. Both isomers are crystalline solids.

STEP Fb

Preparation of 7'β

Following the procedure of Step Fa, except replacing the starting material 6'α with 6'β isomer, the products, trans-7'β (4.0 g) and cis-7'β (0.1 g), are obtained.

STEP Fc

Preparation of 7''β

Under anhydrous conditions at 0° C. a solution of R enriched trans-7'β (2.90 g) in 60 ml methylene chloride is treated 4-dimethylaminopyridine (3.32 g) and o-nitrobenzylchloroformate (5.88 g). The mixture is allowed to warm to room temperature and stirred for 1 hr. The resulting mixture is washed with 0.1 N Hcl, water, brine and water. The organic layer is separated, dried over Na₂SO₄ and allowed to evaporate in vacuo to give crude products. The crude products dissolved in 20 ml ether and chilled at −5° C. give the o-nitrobenzyl alcohol (0.5 g) which is separated by filtration. The isomeric mixture trans-7″β is purified and separated by HPLC (silica gel) eluting with 40% ethylacetate/cyclohexane to give 1.2 g of S-trans-7″β and 1.0 g of R-trans-7″β.

The p-nitrobenzyloxycarbonyl protected species is prepared in an analogous way using p-nitrobenzylchloroformate.

The spectra data of R-trans-7″β:
NMR (300 MHz, CDCl₃): 1.12 (d), 1.40 (s), 1.46 (d), 1.73 (s), 1.95 (m), 3.20 (q), 3.60 (q), 3.74 (q), 3.95 (q), 5.07 (m), 5.58 (q), 7.56 (t), 7.70 (m) and 8.19 (d) ppm.

The spectra data of S-trans-7″β:
NMR (300 MHz, CDCl₃): 1.10 (d), 1.40 (s), 1.43 (d), 1.72 (s), 1.94 (m), 3.34 (q), 3.61 (q), 3.67 (q), 3.96 (q), 5.13 (m), 5.64 (d), 7.53 (m), 7.68 (m), and 8.17 (d) ppm.

STEP Fd

Preparation of 7″α

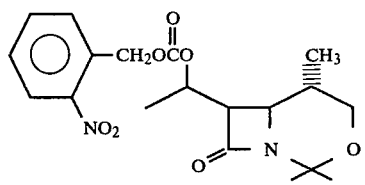

Following the procedure of Step Fc; except replacing the starting material trans-7′β with trans-7′α isomer, the products R-trans-7″α and S-trans-7″α are obtained.

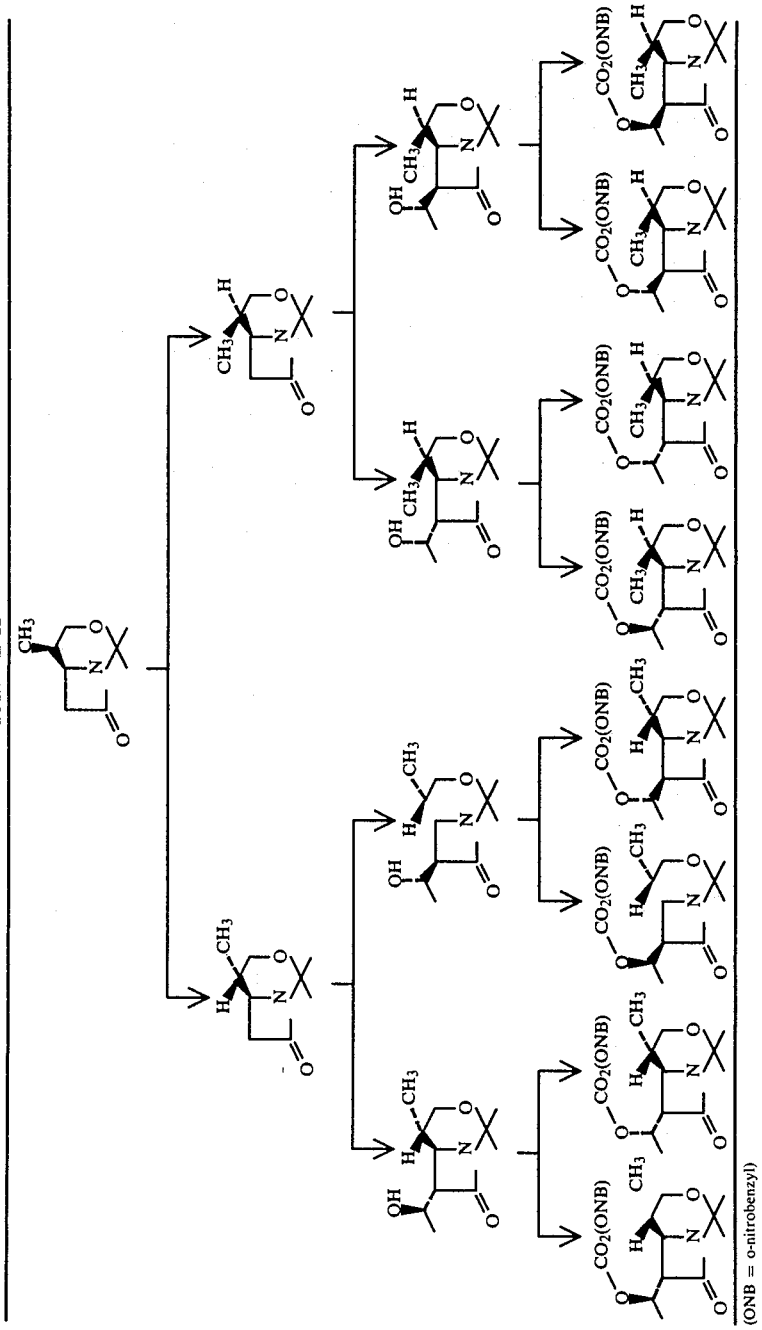

STEP Ga

Preparation of R-trans-9'β:

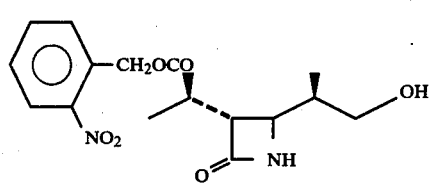

R-trans-9'β

8-Oxo-3-oxa-5β-2,2-trimethyl-7α-(1R-o-nitrobenzyl-carbonyldioxyethyl)-1-azabicyclo-[4.2.0]octane (R-trans-7"β) (2.1 g) is dissolved in 4 ml trifluoroacetic acid and 4 ml water at room temperature and the mixture is stirred for 10 minutes. The resulting homogeneous solution is slowly poured into a vigorously stirred saturated solution of potassium bicarbonate (30 ml) in a 200-ml beaker. The mixture is extracted with methylene chloride (200 ml). The organic layer is separated, dried over Na₂SO₄ and allowed to evaporate in vacuo to give crude product 9' which is purified by a silica gel column eluting with 40% ethylacetate/cyclohexane to afford product R-trans-9'β as an oil, NMR (300 MHz, CDCl₃): 0.98 (d), 1.28 (d), 2.85 (m), 3.20 (q), 3.62 (m), 5.12 (m), 5.57 (q), 6.40 (s), 7.53 (t), 7.66 (m) and 8.14 (d).

Step Gb

Following the procedure of Step Gb, except systematically replacing the starting material with the other isomers, the other isomeric products are obtained (Table III). (R is o- or p-nitrobenzyloxycarbonyl.)

TABLE III

| Starting material | | Product | |
|---|---|---|---|
| (structure) | S-trans-7"β | (structure) | S-trans-9'β |
| (structure) | R-trans-7"α | (structure) | R-trans-9'α |
| (structure) | S-trans-7"α | (structure) | S-trans-9'α |
| (structure) | R-cis-7"α | (structure) | R-cis-9'α |
| (structure) | S-cis-7"α | (structure) | S-cis-9'α |
| (structure) | R-cis-7"β | (structure) | R-cis-9'β |

TABLE III-continued

| Starting material | | Product | |
|---|---|---|---|
| (structure) | S-cis-7"β | (structure) | S-cis-9'β |

STEPS H-K

Steps H-K complement Steps E, Fa-d, G for the preparation of 3-(1-p-nitrobenzylcarbonyldioxyethyl)-4-(1-methyl-2-hydroxyethyl)azetidinone

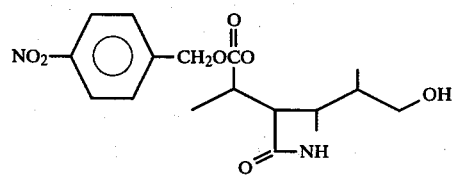

STEP H

Preparation of 1-(2-Tetrahydropyranyl)-4-[1-methyl-2-(2-tetrahydropyranyl)oxyethyl]-2-azetidinone

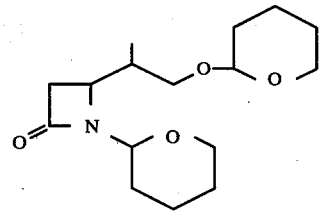

Under nitrogen and at 25° C., a solution of 4-(1-methyl-2-hydroxyethyl)-2-azetidinone (62 mg), in 0.5 ml of anhydrous p-dioxane is treated with 2,3-dihydropyran (0.98 ml) and p-toluenesulfonic acid monohydrate (19 mg). The resulting solution is stirred for a period of 60 minutes and then partitioned between 10 ml of 0.5 M pH 7 phosphate buffer and 10 ml of ethyl acetate. The aqueous phase is extracted a second time with ethyl acetate. The combined ethyl acetate solutions are washed with brine, dried over magnesium sulfate and filtered. The filtrate is evaporated under reduced pressure to give 216 mg of crude product. Purification by preparative thick-layer chromatography developing with ethyl acetate gives 80 mg of 1-(2-tetrahydropyranyl)-4-[1-methyl-2-(2-tetrahydropyranyl)-oxyethyl]-2-azetidinone as an oil.

STEP I

Preparation of Cis and Trans-1-(2-tetrahydropyranyl)-3-(1-hydroxyethyl)-4-[1-methyl-2-(2-tetrahydropyranyl)-oxyethyl]-2-azetidinone

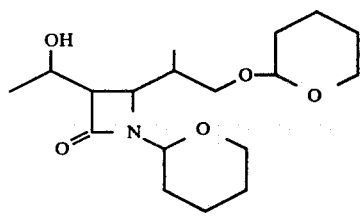

Following the procedure described for the preparation of 8-oxo-2,2,5-trimethyl-7α and β(1-hydroxyethyl)-3-oxa-1-azabicyclo[4.2.0]octane from 8-oxo-2,2,5-trimethyl-3-oxa-1-azabicyclo[4.2.0]octane and using 1-(2-tetrahydropyranyl)-4-[1-methyl-2-(2-tetrahydropyranyl)oxyethyl]-2-azetidinone one obtains a diastereomeric mixture of both cis and trans-1-(2-tetrahydropyranyl)-3-(1-hydroxyethyl)-4-[1-methyl-2-(2-tetrahydropyranyl)oxyethyl]-2-azetidinone.

STEP J

Preparation of Cis and Trans-1-(2-tetrahydropyranyl)-3-(1-p-nitrobenzylcarbonyldioxyethyl)-4-[1-methyl-2-(2-tetrahydropyranyl-)oxyethyl]-2-azetidinone

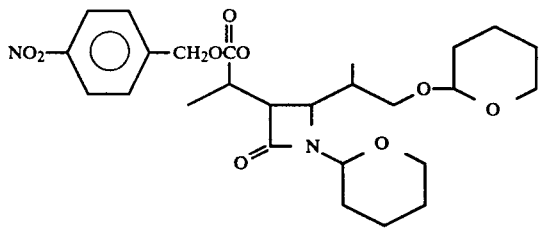

Following the procedure described for the preparation of 8-oxo-2,2,5-trimethyl-7α-(1-p-nitrobenzylcarbonyldioxyethyl)-3-oxa-1-azabicyclo[4.2.0]octane from 8-oxo-2,2,5-trimethyl-7α-(1-hydroxyethyl)-3-oxa-1-azabicyclo[4.2.0]octane and using trans-1-(2-tetrahydropyranyl)-3-(1-hydroxyethyl)-4-[1-methyl-2-(2-tetrahydropyranyl)oxyethyl]-2-acetidinone there is obtained trans-1-(2-tetrahydropyranyl)-3-(1-p-nitrobenzylcarbonyldioxyethyl)-4-[1-methyl-2-(2-tetrahydropyranyl)oxyethyl]-2-acetidinone. The cis diastereoisomers are obtained in an analogous manner.

STEP K

Preparation of Cis and Trans-3-(1-p-nitrobenzylcarbonyldioxyethyl)-4-(1-methyl-2-hydroxyethyl)-2-azetidinone

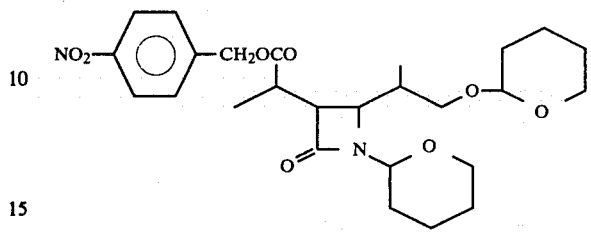

A solution of trans-1-(2-tetrahydropyranyl)-3-(1-p-nitrobenzylcarbonyldioxyethyl)-4-[1-methyl-2-(2-tetrahydropyranyl)oxyethyl]-2-azetidinone in methanol at 25° C. is treated with 0.1 molar equivalent of p-toluenesulfonic acid monohydrate. The solution is stirred for a period of 2 hours and then neutralized with 1 M pH 7 phosphate buffer. The product is extracted into ethyl acetate. The ethyl acetate solution is washed with brine, dried over magnesium sulfate and filtered. The filtrate is evaporated under reduced pressure to give trans-3-(1-p-nitrobenzylcarbonyldioxyethyl)-4-(1-methyl-2-hydroxyethyl)-2-azetidinone. The cis diastereoisomers are obtained in an analogous manner.

STEP L

Preparation of 12

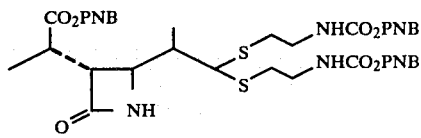

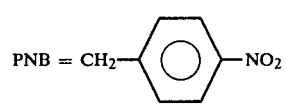

To 6.75 ml anhydrous pyridine (83.9 mmole) in 350 ml anhydrous acetonitrile is added 4.05 g anhydrous powedered chromium trioxide. After stirring at room temperature (25° C.) for 30 minutes, 9.6 g dried Supercell is added and stirring is continued for 5 additional minutes. A solution of 3.21 g trans-3-(1-p-nitrobenzylcarbonyldioxyethyl)-4-(1-methyl-2-hydroxyethyl)-2-azetidinone in 30 ml anhydrous acetonitrile is added all at once. The reaction mixture is stirred under anhydrous conditions at room temperature (25° C.) for one hour. Addition of 9.6 g NaHSO$_3$ is followed by 5 minutes of stirring after which the reaction mixture is filtered through a mixed packed bed of 40 g silica gel and 40 g anhydrous magnesium sulfate. The bed is washed repeatedly with acetonitrile (total volume of filtrate 600 ml). The filtrate is concentrated under a N$_2$ stream to 130 ml total volume. To this solution containing crude aldehyde at 0° C. under N$_2$ is added 9.64 g p-nitrobenzyloxycarbonylaminoethanethiol as prepared below (Step M). To the stirred reaction mixture is added 8.0 ml boron trifluoride etherate (63.4 mmole). After 1.5 hours at 0° C. the reaction mixture is poured into a stirred ice-cold mixture of 69 g K$_2$HPO$_4$-500 ml H$_2$O and 700 ml ethyl acetate (EA). The layers are separated, and the aqueous one is saturated with NaCl and re-extracted with additional EA. The combined organic layers are washed twice with brine, dried over anhydrous MgSO4 and filtered. The filtrate is concentrated under a N2 stream and then pumped on high vacuum to give crude 12.

The material is chromatographed on 450 g silica gel (column height=48 cm; diameter=5.5 cm) packed and applied in CHCl3 and eluted with increasing percentages of MeOH in CHCl3 (0-4% MeOH/CHCl3). Those fractions containing the desired product are combined, concentrated under a N2 stream; and pumped on high vacuum to give 12.

STEP M

Preparation of p-Nitrobenzyloxycarbonylaminoethanethiol

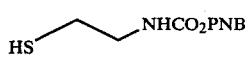

To 600 ml diethyl ether (Et2O)-75 ml H2O in an ice bath with stirring is added 3.2 g cysteamine hydrochloride (mw=114; 28.1 mmole). A solution of 7.14 g NaHCO3 (mw=84; 85 mmole) in 75 ml H2O is added. The ice bath is removed, and at room temperature a solution of 6.75 g p-nitrobenzylchloroformate (mw=216; 31.3 mmole) in 270 ml Et2O is added dropwise over a period of one hour. After 10 additional minutes. the layers are separated. The ether layer is extracted with 150 ml 0.25 HCl, and then with 200 ml brine. Each aqueous layer is then backwashed successively with 100 ml Et2O. The combined ET2O layers are dried over anhydrous MgSO4, filtered, and concentrated under a N2 stream. The crystalline residue is slurried in a small amount of ether, filtered, and the pale yellow crystals are dried under high vacuum to give 4.7 g p-nitrobenzyloxycarbonylaminoethanethiol.

NMR (CDCl3) 8.18 (d, J=8 Hz, aromatic protons ortho to nitro), 7.47 (d, J=8 Hz, aromatic protons meta to nitro), 5.27 (—NH—), 5.20 (s, —CH2—φ-pNO2), 3.40 (m, —CH2—NH—), 2.67 (m, —CH2—SH), 1.35 (t, J=8.5 Hz, —SH) in ppm downfield from TMS.

IR (CHCl3 solution) carbonyl-1725 cm$^{-1}$

M.S.-molecular ion-256, (M-47) at 209 (M-136) at 120, +CH2φpNO2 at 136.

STEP N

Preparation of 14

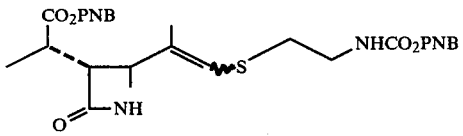

To 14.2 ml pentane (dried over 4A Linde molecular sieves) is added 0.5 ml Br2. To 5 g of 12 in 58 ml tetrahydrofuran (THF) (freshly distilled from lithium aluminum hydride (LAH) and 65 ml Et2O (dried over 3A 1/16" Linde molecular sieves) at 0° C. under N2 with stirring is added dropwise 10 ml of the above 0.66 M Br2 solution. After 10 minutes at 0° C., 0.67 ml cyclohexene is added. After 5 minutes at 0° C., 1.7 ml triethylamine is added immediately followed by 40 ml ice-cold dimethylformamide (DMF) (distilled from anhydrous CaSO4 at 40 mm and stored over 4A Linde molecular sieves). The ice bath is removed, and stirring is continued for 2¼ hours at room temperature. The reaction mixture is poured into a stirred ice-cold mixture of 12.6 ml 1 M KH2PO4 160 ml H2O-500 ml (EA). After separation of the layers, the aqueous one is saturated with sodium chloride and re-extracted with EA. The combined organic layers are extracted once with brine, dried over anhydrous MgSO4, filtered and concentrated under a N2 stream followed by pumping under high vacuum to provide crude 14.

The material is chromatographed on 250 g silica gel (height=45 cm; diameter=4.5 cm) packed and applied in CHCl3 and eluted with increasing percentages of MeOH in CHCl3 (0-3% MeOH/CHCl3). Those fractions containing clean product are combined, concentrated under a N2 stream, and pumped on high vacuum to give 14.

STEP O

Preparation of 15

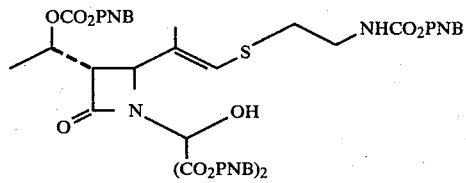

To a stirred solution of 2.48 g di(p-nitrobenzyl)-ketomalonate (Step p) in 400 ml hot anhydrous toluene is added a solution of 2.52 g of 14 in 20 ml THF (distilled from LAH) and 40 ml anhydrous toluene. After some of the solvent is boiled off, additional anhydrous toluene is added, and the azeodrying process is repeated three times. The solution is then refluxed under N2 for 30 minutes. Additional tolune is then allowed to boil off yet the volume is not allowed to diminish so much that precipitation occurs. Total heating time is approximately 2½ hours. The clear yellow reaction mixture is removed from the oil bath and placed under a stream of N2. After concentration to a oil, the residue is dissolved in CH2Cl2, dried over anhydrous MgSO4, filtered, and concentrated under N2 stream to give crude 15.

The material is chromatographed on 250 g silica gel packed and applied in CHCl3 (height=43 cm; diameter=4.5 cm). Elution with 500 ml 0.5% MeOH/CHCl3 is followed by continued elution with 1% MeOH/CHCl3 for the remainder of the chromatography. After the emergence of excess reagent, those fractions containing pure 15 are combined, concentrated under a N2 stream and then on high vacuum to give 15.

STEP P

Preparation of di-p-Nitrobenzyl Ketomalonate

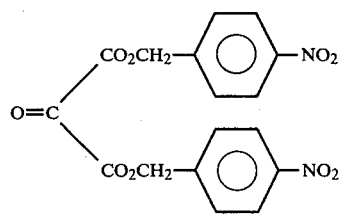

A mixture of 100 g p-nitrobenzyl bromide (0.46 mole), 28.6 g malonic acid (0.275 mole) and 750 ml ethanol (EtOH) is stirred and warmed on the steam bath until solution is achieved. A solution of 33 g KOH in 200 ml of water is added carefully with swirling. An additional 200 ml of water is added, and the two-phase system is refluxed for 1.8 hours. The lighter color homogeneous solution is cooled in ice for 1 hour and the crude product isolated by filtration, washed twice with a minimum of cold EtOH, and dried by pulling dry $N_2$ through the cake; 33.7 g of solid is obtained. If, during the refluxing stage the reaction mixture is slowly concentrated to ca. half volume by allowing refluxing solvent to distill off, the crude product yield rises to 77 g. The material is recrystallized from methanol to give pure di-p-nitrobenzyl malonate.

A mixture of 23.4 of di-p-nitrobenzyl malonate 10 g $SeO_2$, and 30–40 ml of xylene is stirred in a flask immersed in an oil bath The bath temperature is raised over 1 hour to 130°–135°. A gradual darkening of the reaction mixture is noted, and after a total of 4 hours at 130°–135°, most of the insoluble residue is black Se°. The mixture is cooled, $MgSO_4$ is added to remove the water, and Celite is added to aid in filtration. The mixture is filtered through Celite and the cake washed with xylene and a small portion of EtOAc. Final volume: 60 ml. A 100 g column of Baker silica gel is prepared in benzene and 10 ml of filtrate applied, then eluted with increasing amount of EtOAc in benzene, 500 ml fractions being collected. After one 2% ethyl acetate (EtOAc)/$\phi$H, and two 10% EtOAc/$\phi$H fractions, the third 10% and first 20% EtOAc/$\phi$H provide the bulk of the product (1.6 g from 10 ml filtrate) and judged by tlc (20% EtOAc/$CHCl_3$; silica gel GF). Recrystallization from benzene, (1 g in ca. 50 ml concentrated to $\frac{1}{2}$ volume and "spiked" with 1 ml of $H_2O$ saturated benzene) provides di-p-nitrobenzyl ketomalonate. ($\phi$H=benzene.)

Step Q

Preparation of 17:

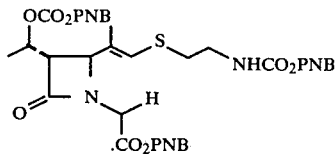

A solution of 1.468 g of 15 in $CH_2Cl_2$ is dried over anhydrous $MgSO_4$, filtered, and concentrated under a $N_2$ stream, and dried further under high vacuum just prior to the following reaction. To a solution of 15 in 24 ml THF (freshly distilled from LAH) at −20° C. is added 0.206 ml anhydrous pyridine. With stirring under $N_2$, 294 mg of freshly distilled thionyl chloride in 5 ml THF is added dropwise. The reaction mixture is stirred for 10 minutes at −20° C., then $\frac{1}{2}$ hour at 0° C. and finally 1 hour at 25° C. The pyridine hydrochloride is filtered under $N_2$ and washed with 20 ml THF. The filtrate is concentrated under $N_2$ stream followed by pumping on high vacuum.

To this freshly prepared chloro compound is added with stirring a freshly shaken suspension of 678 mg tributylphosphine in 36.5 ml 9:1 DMF-$H_2O$ followed gy 294 mg $K_2HPO_4$. The reaction mixture is stirred at 25° C., for 35 minutes. After dilution with 120 ml EA and 60 ml brine, the layers are separated, and the aqueous one is extracted two times with EA. The combined organic layers are washed one time with brine, dried over anhydrous $MgSO_4$, filtered and concentrated under a $N_2$ stream followed by pumping on high vacuum to give crude 17.

The material is chromatographed on 100 g silica gel (height=28.5 cm; d=4 cm) packed and applied in $CHCl_3$ and eluted with 0.5% MeOH in $CHCl_3$. Those fractions containing clean product are combined, concentrated under a $N_2$ stream and then on high vacuum to give 17. (EA=ethyl acetate.)

STEP R

Preparation of 19

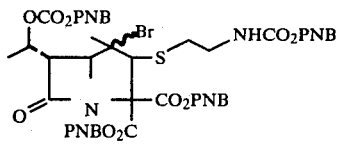

To 8.5 ml pentane (dried over 4A Linde molecuar sieves) is added 0.2 ml $Br_2$. To 0.706 g of 17 in 18 ml THF (freshly distilled from LAH) and 5.7 ml $Et_2O$ (dried over 3A 1/16" Linde molecular sieves) at 0° C. under $N_2$ with stirring is added dropwise 1.8 ml of the above 0.45 M $Br_2$ solution (0.81 mmole). After 15 minutes at 0° C., 0.42 ml triethylamine is added immediately followed by 10.5 ml ice-cold DMF (distilled from $CaSO_4$ at 40 mm and stored over 4A Linde molecular sieves). The ice-bath is removed, and stirring at room temperature is continued for 2 hours. The reaction mixture is poured into a stirred ice-cold mixture of 2.1 ml 1 M $KH_2PO_4$-70 ml $H_2O$-100 ml EA. The layers are separated, and the aqueous one is saturated with NaCl and re-extracted with EA. The combined organic layers are washed once with brine, dried over anhydrous $MgSO_4$, and filtered. The filtrate is concentrated under a $N_2$ stream and then pumped on high vacuum to give crude 19.

The material is chromatographed on 60 g silica gel (diameter=2.8 cm) packed and applied in $CHCl_3$ and is eluted with 100 ml-2% EA/$CHCl_3$; 100 ml-4% EA/$CHCl_3$ and then 5% EA/$CHCl_3$ for the remainder of the chromatographed. The fractions containing pure 19 are combined, concentrated under a $N_2$ stream, and pumped on high vacuum to give 19.

STEP S

Preparation of 20:

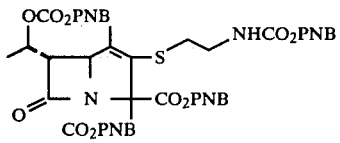

To 29 mg anhydrous silver fluoride is added a solution of 146 mg of 19 in 3.5 ml anhydrous pyridine. The stoppered reaction mixture is stirred at room temperature in the dark for one hour and then poured into 20 ml cold water-30 ml EA. After separation of the layers, the aqueous one is extracted two times with EA and one time with $CHCl_3$. Each organic layer is extracted one time with $H_2O$ and one time with brine. The combined organic layers are dried over anhydrous $MgSO_4$, filtered, and concentrated under a N₂ stream followed by pumping on high vacuum to give crude 20.

Preparative thin layer chromatography (eluant=40% acetone/hexane; repeated extraction of desired u.v. band with a large volume of CHCl₃) yields slightly contaminated 20. Re-chromatographing on silica using EA in CHCl₃ as an eluting system gives pure 20.

STEP T

Preparation of 21:

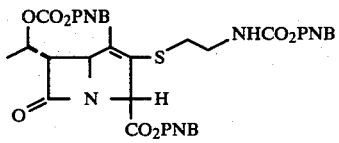

A solution of 77 mg of 20 in 0.9 ml S-collidine (distilled from powdered KOH) is added to 13.4 mg anhydrous LiI (dried for few hours at 100° C. over P₂O₅ under vacuum). With stirring under N₂, the reaction mixture is heated in an oil bath at 120° C. After a total of 30 minutes, the reaction mixture is cooled to 25° C., diluted with CH₂Cl₂, and transferred to a round bottom flask for concentration under a N₂ stream and then on high vacuum. Partitioning the residue between EA-H₂O and 1 ml 1 M KH₂PO₄ is followed by extraction of the aqueous layer two additional times with EA and one time with CHCl₃. Each organic layer is then backwashed with brine. The combined organic layers are dried over anhydrous MgSO₄ filtered, concentrated under a N₂ stream and then on high vacuum to give crude 21.

Preparative thin layer chromatography on silica gel yields 21.

STEP U

Preparation of 22:

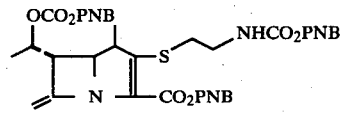

To 49 mg of 21 in 0.7 ml DMSO (distilled from CaH₂ at 8 mm and stored over 4A Linde molecular sieves) is added 100 μl diisopropylamine (distilled from NaH under N₂ and stored over 4A Linde molecular sieves). The stoppered reaction mixture is stirred for a few minutes and tehn allowed to stand for 2 hours. The amine and most of the DMSO are then concentrated off under high vacuum with no external heating. The residue is passed quickly through a column of silica gel (packed, applied and eluted with EA) to remove residual DMSO. After concentration under a N₂ stream of all fractions having u.v. absorbance, the material is chromatographed on a thin layer silica gel plate (eluant=50% EA/CHCl₃; repeated extraction of desired u.v. bands with a large volume of chloroform) to give 22.

STEP V

Preparation of I:

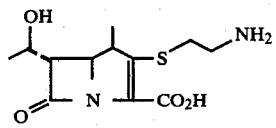

To 5.2 mg 22 is added 0.60 ml dioxane, 0.05 ml ethanol, 0.35 ml deionized water and 0.01 ml of 1.0 M K₂HPO₄. To the resultant clear solution is added 5 mg of 10% Pd/C. The suspension is flushed with N₂, then closed under 50 psi H₂ atmosphere for 30–40 minutes. After centrifugation, the Pd/C is washed and centrifugated with 0.5 ml portions of deionized water. The combined centrifugates are extracted 5× with 2 ml portions ether. Residual ether is removed under vacuum and the aqueous solution is chromatographed on an XAD-2 column (20×140 mm) which is eluted with water to give the desired product I.

EXAMPLE 3

Preparation of Bis (p-Nitrobenzyloxycarbonylaminoethyl)disulfide

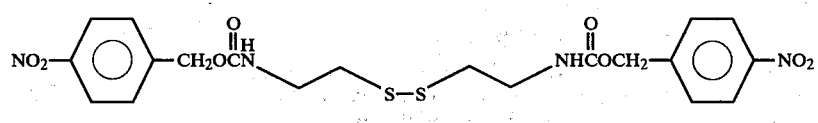

Under nitrogen at −20° C., bromide (1.21 ml, 0.022 mmole) is added to a solution of p-nitrobenzyloxycarbonylaminoethanethiol (11.28 g, 0.044 mole) in 100 ml of anhydrous tetrahydrofuran. The cooling bath is removed, and the cold solution is stirred for 15 minutes. The solution is then diluted with 400 ml ethyl acetate and washed with 200 ml 1 M pH 7 phosphate buffer, 200 ml 1 M dibasic potassium phosphate, water (2×200 ml, 100 ml) and 200 ml brine. It is dried over anhydrous magnesium sulfate and filtered. The filtrate is evaporated in vacuo giving a yellow solid residue. This material is chromatographed on silica gel eluting with 5% ethyl acetate/chloroform to give 10.5 g of crystalline bis (p-nitrobenzyloxycarbonylaminoethyl)disulfide:

| | |
|---|---|
| IR (CH₂Cl₂) μ : | 3.04 NH |
| | 5.96 carbonyl |
| | 6.22, 6.61 nitro |
| NMR (CDCl₃) : | 8.24 ⎫ |
| | ⎬ d, J = 8.5Hz, ArH |
| | 7.54 ⎭ |
| | 5.37, broad s. NH |
| | 5.26, s, ArCH₂O |
| | 3.60, q, J = 6Hz and 6Hz, NHCH₂CH₂ |
| | 2.86, t, J = 6Hz, NHCH₂CH₂S. |

EXAMPLE 4

Following the procedure of Example 2, Steps A-Gb, the following substituted azetidinones 10 are obtained when an equivalent amount of the appropriately substituted butadiene reagent is substituted for the 1-acetoxyl-2-methyl-1,3-butadiene of Example 2, Step A. The following chart gives the final azetidinone product, and necessary reagents. (Ph=phenyl.)

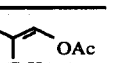

| Compound | R | R¹ | Butadiene in Step A |
|---|---|---|---|
| 1. | COOCH₂-⟨O⟩-NO₂ | CH₃CH₂— | OAc, C₂H₅ |
| 2. | COOCH₂-⟨O⟩-NO₂ | CH₃CH₂CH₂ | OAc, C₃H₇ |
| 3. | COOCH₂-⟨O⟩-NO₂ | (CH₃)₂CH— | OAc |
| 4. | COOCH₂-⟨O⟩-NO₂ | ▷— | ⟨cyclopropyl⟩OAc |
| 5. | COOCH₂-⟨O⟩-NO₂ | Ph— | OAc, Ph |
| 6. | COOCH₂-⟨O⟩-NO₂ | PhCH₂— | OAc, CH₂Ph |

EXAMPLE 5

Following the procedure of Example 2, Steps L-V, the following species of the present invention are obtained when the azetidinones 10 of Example 4 are substituted in equivalent amounts, respectively, for the azetidinone of Example 2, Step L. The products of this Example are presented in the tabular fashion below:

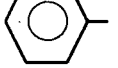

| Compound | R¹ | Remarks |
|---|---|---|
| 1. | CH₃CH₂— | |
| 2. | CH₃CH₂CH₂— | |
| 3. | (CH₃)₂CH— | |
| 4. | ▷— | |
| 5. | ⟨phenyl⟩— | |
| 6. | ⟨phenyl⟩—CH₂— | |

EXAMPLE 6

Preparation of Pharmaceutical Compositions

One such unit dosage form is prepared by mixing 120 mg of 1-methyl-6-(1-hydroxyethyl)-2-(2-aminoethylthio)-1-carbadethiapen-2em-3-carboxylic acid with 20 mg of lactose and 5 mg of magnesium stearate. The 145 mg. mixture is placed into a No. 3 gelatin capsule. Similarly, by employing more of the active ingredient and less lactose, other dosage forms can be put up in No. 3 gelatin capsules and should it be necessary to mix more than 145 mg. of ingredients together larger capsules such as compressed tablets and pills can also be prepared. The following examples are illustrative of the preparation of pharmaceutical formulations:

| TABLET | PER TABLET |
|---|---|
| 1-methyl-6-(1-hydroxyethyl)-2-(2-aminoethylthio)-1-carbadethiapen-2-em-3-carboxylic acid | 125 mg. |
| Dicalcium Phosphate | 192 mg. |
| Cornstarch, U.S.P. | 6 mg. |
| Lactose, U.S.P. | 190 mg. |
| Magnesium Stearate | Balance |

The active ingredient is blended with the dicalcium phosphte, lactose and about half of the cornstarch. The mixture is then granulated with 15% cornstarch paste (6 mg) and rough-screened. It is dried at 45° C. and screened again through No. 16 screens. The balance of the cornstarch and the magnesium stearate is added and the mixture is compressed into tablets, approximately 0.5 inch in diameter each weighing 800 mg.

| PARENTERAL SOLUTION | |
|---|---|
| Ampoule: | |
| 1-methyl-6-(1-hydroxyethyl)-2-(2-aminoethylthio)-1-carbadethiapen-2-em-3-carboxylic acid | 500 mg. |
| Diluent: Sterile Water for Injection | 5 cc |
| OPTHALMIC SOLUTION | |
| 1-methyl-6-(1-hydroxyethyl)-2-(2-aminoethylthio)-1-carbadethiapen-2-em-3-carboxylic acid | 100 mg. |
| Hydroxypropylmethyl cellulose | 5 mg. |
| Sterile water to | 1 ml. |
| OTIC SOLUTION | |
| 1-methyl-6-(1-hydroxyethyl)-2-(2-aminoethylthio)-1-carbadethiapen-2-em-3-carboxylic acid | 100 mg. |
| Benzalkonium chloride | 0.1 mg. |
| Sterile water to | 1 ml. |
| TOPICAL OINTMENT | |
| 1-methyl-6-(1-hydroxyethyl)-2-(2-aminoethylthio)-1-carbadethiapen-2-em-3-carboxylic acid | 100 mg. |
| Polyethylene Glycol 4000 U.S.P. | 400 mg. |
| Polyethylene Glycol 400 U.S.P. | 1.0 gram. |

The active ingredient in the above formulations may be administered alone or in combination with other biologically active ingredients as, for example, with other antibacterial agents such as lincomycin, a penicillin, streptomycin, novobiocin, gentamicin, neomycin, colistin and kanamycin, or with other therapeutic agents such as probenecid.

What is claimed is:

1. A compound having the formula:

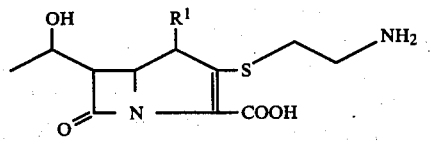

and its pharmaceutically acceptable salts wherein $R^1$ is selected from the group consisting of substituted and unsubstituted loweralkyl having from 1-6 carbon atoms, phenyl, phenylloweralkyl, cycloalkyl having from 3 to 6 carbon atoms, and cycloalkylalkyl having 4 to 7 carbon atoms in the chain and 3-6 carbon atoms in the ring; wherein said substituents on $R^1$ are selected from the group consisting of halogen, hydroxyl, amino, alkyl having 1-6 carbon atoms, azido, cyano, and carboxyl.

2. A compound according to claim 1 wherein $R^1$ is methyl, phenyl, benzyl, ethyl, cyclopropyl, propyl and isopropyl.

3. A compound according to claim 2 wherein $R^1$ is methyl having the structure

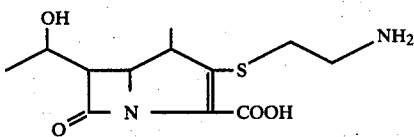

4. A compound having the formula:

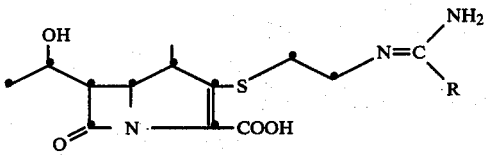

wherein R is H or $CH_3$.

5. An antibiotic pharmaceutical composition comprising a therapeutically effective amount of a compound according to claim 1, 2, 3, or 4 and a pharmaceutically carrier therefor.

* * * * *